(12) United States Patent
Heinz (10) Patent No.: US 9,220,844 B2
(45) Date of Patent: Dec. 29, 2015

(54) SYRINGE HAVING REDUCED STATIC FRICTION

(75) Inventor: Jochen Heinz, Flintbeck (DE)

(73) Assignee: Transcodent GmbH & Co. KG, Kiel (DE)

( * ) Notice: Subject to any disclaimer, the term of this patent is extended or adjusted under 35 U.S.C. 154(b) by 174 days.

(21) Appl. No.: 13/810,232

(22) PCT Filed: Jun. 20, 2011

(86) PCT No.: PCT/EP2011/060189
§ 371 (c)(1),
(2), (4) Date: Jan. 15, 2013

(87) PCT Pub. No.: WO2012/007251
PCT Pub. Date: Jan. 19, 2012

(65) Prior Publication Data
US 2013/0116627 A1    May 9, 2013

(30) Foreign Application Priority Data
Jul. 15, 2010   (DE) .......................... 10 2010 027 243

(51) Int. Cl.
*A61M 5/00*    (2006.01)
*A61M 5/315*   (2006.01)

(52) U.S. Cl.
CPC ....... *A61M 5/31513* (2013.01); *A61M 5/31515* (2013.01)

(58) Field of Classification Search
CPC ...................... A61M 5/31513; A61M 5/31515
USPC .................................. 604/218, 221, 222, 230
See application file for complete search history.

(56) References Cited

U.S. PATENT DOCUMENTS 3,718,139 A * 2/1973 Hanford ........................ 604/87
5,478,314 A * 12/1995 Malenchek .................... 604/110
7,087,037 B2 * 8/2006 Chiba et al. .................... 604/38
(Continued)

FOREIGN PATENT DOCUMENTS

DE    102007034477    1/2009
EP    1264611         12/2002
(Continued)

OTHER PUBLICATIONS

Search Report, for Application PCT/EP2011/060189.

*Primary Examiner* — Aarti B Berdichevsky
(74) *Attorney, Agent, or Firm* — Alix, Yale & Ristas, LLP (57) ABSTRACT

A syringe comprising a cylinder and a plunger arranged in the latter has a sealing element which, with a contact region, abuts an inner wall of the cylinder and seals an annular gap between the plunger and an inner wall of the cylinder. The contact region has a front section which, in the rest state, abuts the inner wall of the cylinder with an abutment pressure. The plunger is connected to the sealing element in such a way that the sealing element does not follow an initial movement of the plunger out of the rest state and such that the sealing element follows a continued movement of the plunger. The abutment pressure between the sealing element and the inner wall in the front section of the contact region decreases during the initial movement. With the syringe, less force is required in order to overcome the static friction between the sealing element and the inner wall of the cylinder.

20 Claims, 5 Drawing Sheets

(56) References Cited

U.S. PATENT DOCUMENTS

| | | | |
|---|---|---|---|
| 8,641,416 B2 * | 2/2014 | Leiner et al. | 433/90 |
| 2003/0014005 A1 * | 1/2003 | Chiba et al. | 604/38 |
| 2008/0300550 A1 * | 12/2008 | Schiller et al. | 604/220 |
| 2009/0047622 A1 * | 2/2009 | Leiner et al. | 433/90 |
| 2010/0016807 A1 * | 1/2010 | Thilly | 604/218 |

FOREIGN PATENT DOCUMENTS

| | | |
|---|---|---|
| EP | 2016962 | 1/2009 |
| GB | 1168201 | 10/1969 |
| GB | 1260103 | 1/1972 |
| GB | WO2007116086 | 10/2007 |

* cited by examiner

SYRINGE HAVING REDUCED STATIC FRICTION

BACKGROUND

The invention relates to a syringe with a cylinder and a plunger arranged within the cylinder. Provision is made for a sealing element, which rests against an inner wall of the cylinder with a contact region and seals an annular gap between the plunger and an inner wall of the cylinder. The contact region has a front section, which, in the rest state, rests against the inner wall of the cylinder with contact pressure. The plunger is connected to the sealing element such that the sealing element does not follow an initial movement of the plunger from the rest state and that the sealing element follows a continued movement of the plunger.

Such syringes serve to eject a liquid or pasty substance in a targeted and metered fashion. By way of example, these syringes are used in medical and dental applications. The substance is contained in an interior of the syringe. As a result of pressure on the plunger said plunger penetrates further into the cylinder, and so the space available to the substance reduces. The substance emerges from the cylinder and is emitted—for example through a hollow needle—at the desired spot.

The sealing element is used to seal the interior of the cylinder such that the substance is prevented from emerging between the plunger and the inner wall of the cylinder. In order to have a sufficient sealing effect, the sealing element rests against the inner wall of the cylinder with contact pressure. When the syringe is in the rest state, the result of the contact pressure is static friction between the sealing element and the inner wall of the cylinder. It is well known that the static friction between two surfaces at rest relative to one another is greater than the dynamic friction between two surfaces that move relative to one another. When the syringe is operated, it is initially necessary to overcome the static friction in order to set the sealing element in motion relative to the cylinder. Thus, there is a relatively high initial resistance before the sealing element moves. High initial resistance when operating the syringe is first of all not very user friendly. Secondly, sudden breaking free of the plunger can lead to the contents of the syringe emerging in an uncontrolled manner.

SUMMARY

Proceeding from this prior art, a syringe with an improved user friendliness is presented. The contact pressure between the front section of the contact region and the inner wall of the cylinder is reduced during an initial movement of the plunger.

To start with, a few terms will be explained. When the syringe is in the rest state the plunger does not move relative to the cylinder. The sealing element rests against the inner wall of the cylinder over the circumference of the plunger, with there being sufficient contact pressure for the interior of the syringe to be sealed. Starting from the rest state, the plunger can carry out an initial movement without the sealing element following the initial movement.

When observed in the longitudinal direction of the syringe, the contact region between the sealing element and the inner wall of the cylinder has an extent extending from a rear end to a front end. The front end points in the direction in which the substance emerges from the syringe, i.e., to the outlet end. The rear end points in the direction from which the syringe is operated, i.e., at which end pressure is exerted on the plunger when operating the syringe. The term front section of the contact region denotes the front end and the directly adjacent section of the contact region.

The term initial movement relates to a movement of the plunger relative to the cylinder and denotes a movement in the direction of the outlet end of the syringe, which proceeds from the rest state. A continued movement follows an initial movement.

When the contact pressure between the sealing element and the inner wall of the cylinder is reduced, this is generally accompanied by a front section of the contact region being lifted from the inner wall. There then no longer is contact pressure between the sealing element and the inner wall in the front section of the contact region. In an extreme case, the areal regions resting on one another can also remain unchanged and it is merely the contact pressure in the front section of the contact region that reduces to a value not equal to zero. In another extreme case, the contact region is completely lifted off from the inner wall, which is necessarily accompanied by no contact pressure existing anymore in the front section of the contact region as well. This can be considered particularly when the sealing element has a number of mutually separate contact regions.

The static friction that needs to be overcome in order, from the rest state, to set the sealing element into relative motion with respect to the cylinder results to a significant extent from the contact pressure in the front section of the contact region. If the contact pressure in the front section of the contact region is reduced, this significantly reduces the static friction between the sealing element and the inner wall of the cylinder and it is easier to set the sealing element into motion.

An initial movement, which can occur between the plunger and the cylinder without the sealing element moving at the same time, is used to reduce the contact pressure in the front section of the contact region. Thus, the initial movement modifies the force transmission between the plunger and the front contact region such that the front section of the contact region rests against the inner wall of the cylinder with reduced pressure.

In the rest state, the syringe is also leak-proof over a relatively long period of time, which is achieved by virtue of the fact that the sealing element rests against the inner wall of the cylinder with sufficient contact pressure. Although the contact pressure may no longer be sufficient in this sense after the initial movement, i.e., no longer be sufficient to keep the syringe permanently leak-proof, this can be accepted because this only relates to a brief period of time and the sealing element can readily be designed such that the substance can nevertheless be reliably ejected from the syringe. The invention differs from syringes as disclosed in DE 10 2007 034 477 A1 by virtue of the reduced contact pressure in the front section of the contact region.

The plunger within the cylinder moves forward with the initial movement, i.e., in the longitudinal direction of the syringe. By contrast, the contact pressure in the front section of the contact region, which should be reduced by the initial movement, acts in the radial direction.

It follows that the movement in the longitudinal direction must be converted such that it results in a modified force transmission in the radial direction. In respect of the specific conversion of this force transmission there are a number of options, some of which will be explained below.

The sealing element can be designed such that it applies sufficient contact pressure on the inner wall of the cylinder without additional external action. By way of example, this can be achieved by virtue of the fact that the sealing element in a relaxed state has a somewhat greater diameter than the cylinder such that it must be slightly compressed in order to be able to be inserted into the cylinder. The invention can provide for a transmission element between the plunger and the sealing element, by means of which force is transmitted onto the sealing element during the initial movement of the plunger in order to reduce the contact pressure. In particular, the transmission element can be embodied such that it transmits a tensile force on the sealing element. For the purpose of an effective transmission of the tensile force, the transmission element can, from the front contact region of the sealing element, extend obliquely toward the front in the direction of the plunger.

The syringe is preferably embodied such that the reduction in the contact pressure brings about a significant reduction in the static friction between the sealing element and the inner wall. By way of example, after the initial movement, the static friction between the contact region and the inner wall can be reduced by at least 10%, preferably by at least 20%, more preferably by at least 30% compared to the rest state. If the assumption is made that, in general, the static friction is approximately 50% to 100% greater than the dynamic friction, the static friction in the syringe is no longer substantially greater than the dynamic friction would be without the reduction of the contact pressure. If provision is made for a plurality of contact regions, the static friction of the whole sealing element preferably reduces by at least 10%, preferably by at least 20%, more preferably by at least 30%.

The sealing element can also be designed such that it per se does not have sufficient contact pressure with respect to the inner wall of the cylinder, but rather that the contact pressure is generated by external action. To this end, the plunger can be designed such that it exerts a radially outwardly acting force on the sealing element in the rest state. The radially outwardly acting force reduces with the initial movement of the plunger. By way of example, to this end, the plunger can be designed to have a conical section such that the sealing element is seated on the thicker end of the cone in the rest state and on the thinner end after the initial movement.

In order to provide the sealing element with the freedom of movement necessary for reducing the contact pressure, there can be a clearance between the sealing element and the plunger in the rest state. The sealing element can move into the clearance during the initial movement of the plunger. In the rest state, there preferably is a clearance particularly in the region which lies radially inward from the front section of the contact region.

With its initial movement, the plunger moves without the sealing element, i.e., the sealing element initially remains in the position it has in the rest state. The syringe can be designed such that the position of the sealing element during this phase is determined solely by the static friction between the sealing element and the inner wall of the cylinder. Alternatively, provision can be made for a sleeve in the annular gap between the plunger and the cylinder, said sleeve guiding the sealing element. Such a sleeve makes the guidance of the sealing element more precise than when the sealing element is held in its position by static friction alone. The sleeve is preferably designed such that it does not move during the initial movement of the plunger. The sleeve can follow a continued movement of the plunger and can be set into motion at the same time as the sealing element. In the longitudinal direction of the syringe, the sleeve can extend from the sealing element to the rear end of the cylinder or further to the rear end of the plunger.

The initial movement, used to reduce the contact pressure in the front section of the contact region, is carried out by the plunger when pressure is exerted on a pressure surface at the rear end of the plunger. In an advantageous embodiment, the syringe is designed such that it independently moves back to the rest position as soon as no pressure is exerted on the pressure surface anymore. This can be achieved by virtue of the fact that the initial movement tensions an elastic element which, after the pressure has dropped off, returns again to its original position and hence moves the plunger into the rest position.

The syringe can be designed such that the transmission element and/or the sealing element itself at the same time act as elastic element which is tensioned by the initial movement. The elastic element can also be a separate element. If a sleeve is provided for guiding the sealing element, the elastic element can engage at one end with the plunger and at the other end with the sleeve.

The sealing element can be designed such that it has a single homogeneous contact region. The sealing element can also have a plurality of mutually separated contact regions, for example in the form of a plurality of sealing lips which are arranged in succession. Then a clearance adjoins the rear end of the front contact region, in which clearance the sealing element does not have contact with the inner wall of the cylinder. The clearance merges into the front section of the next contact region. Particularly if the sealing element comprises a plurality of contact regions, reducing the contact pressure can also consist of one of the contact regions being completely lifted off from the inner wall of the cylinder. Complete lifting off is necessarily accompanied by a reduction in the contact pressure in the front section of the contact region. If one contact region is completely lifted off, this is preferably a rear contact region because otherwise the substance contained in the syringe could enter the region of the stopper.

A preferred application of the syringe involves dental compounds being ejected within the scope of a dental treatment. A further medical field of application lies in injecting active ingredients into the human body. The possible use of syringes according to the invention in crafts or home-improvements as well cannot be excluded.

BRIEF DESCRIPTION OF THE DRAWINGS

The invention will be described in exemplary fashion below on the basis of advantageous embodiments, with reference being made to the attached drawings. In detail.

DETAILED DESCRIPTION

Figure 1:
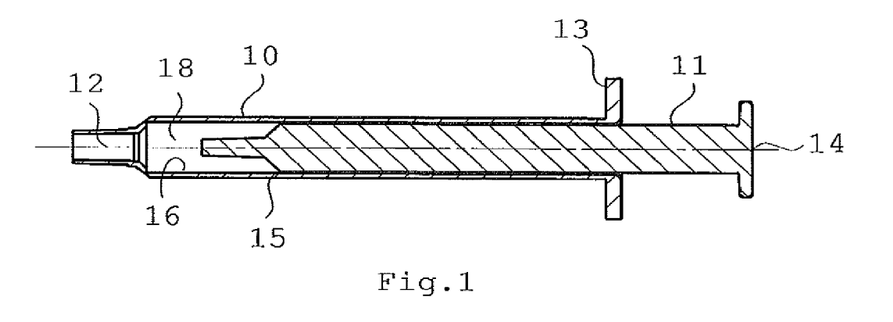
FIG. 1 shows a schematic illustration of a syringe.

A syringe shown in FIG. 1 comprises a syringe body in the form of a cylinder 10, within which a plunger 11 is accommodated. An outlet 12 is formed at the front end of the cylinder 10 and a substance contained in the syringe can emerge therethrough. At its rear end, the cylinder 10 has a collar 13, which protrudes outwardly with respect to the wall of the cylinder 10. The rear end of the plunger 11 is embodied as pressure surface 14, by means of which pressure can be exerted on the plunger 11 in order to set the plunger 11 in relative motion with respect to the cylinder 10. If an operator exerts pressure on the pressure surface 14, the collar 13 can be used as counter bearing.

The interior 23 of the syringe, surrounded by the cylinder 10 and the plunger 11, can be filled by a liquid or pasty substance, which should be ejected through the outlet 12 in a targeted and metered fashion. If the plunger 11 is now set into relative motion with respect to the cylinder 10 by means of pressure on the pressure surface 14, the volume of the interior of the syringe reduces and material emerges toward the front through the outlet 12.

In order to prevent the material from being able to emerge toward the rear through the annular gap 15 between the plunger 11 and the inner wall 16 of the cylinder 10, provision is made for a sealing element (not shown in FIG. 1) which extends around the plunger 11 and seals the annular gap 15. The sealing element rests against the inner face 16 of the cylinder 10 with pressure referred to as contact pressure, and seals this emergence path. In order to set the plunger 11 into motion together with the sealing element, the static friction existing between the sealing element and the inner wall 16 of the cylinder 10 must be overcome. In the case of conventional syringes, this requires increased pressure on the pressure surface 14 of the plunger 11, which is perceived to be not very user friendly. The syringe reduces the force required to set the sealing element into relative motion with respect to the cylinder 10. This renders it possible to set the plunger 11 into motion in a slow and uniform fashion such that the substance also emerges from the syringe in a slow and uniform fashion. A patient into whom an active ingredient is injected finds this more comfortable than jerky breaking free of the plunger 11, by means of which an uncontrolled amount is ejected. The latter can cause pain to the patient.

Figure 2:
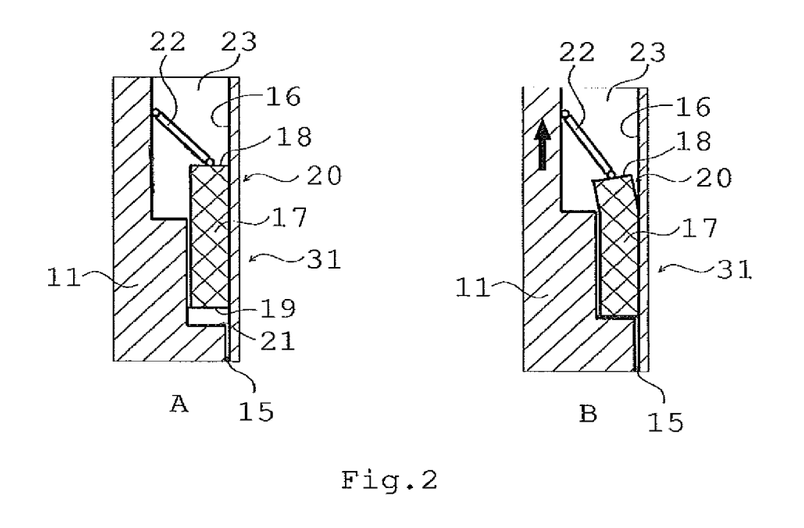
FIGS. 2 to 5 show detailed views of various embodiments.

FIG. 2 shows a section of a first embodiment. In image A, the syringe is in the rest state. The interior 23 is filled with the substance to be ejected. The plunger 11 does not move relative to the cylinder 10 and no pressure is exerted on the pressure surface 14 of the plunger 11. A sealing element 17 extends around the plunger 11 and seals the annular gap 15 between the plunger 11 and the cylinder 10. With its outer lateral surface, the sealing element 17 rests against the inner wall 16 of the cylinder 10 with sufficient contact pressure such that the substance cannot emerge from the syringe, even in the case of long-term storage. The sufficient contact pressure emerges from the shape of the sealing element 17. The lateral surface of the sealing element 17 rests against the inner wall 16 of the cylinder over an area, and so the lateral surface overall forms the contact region 31 between the sealing element 17 and the inner wall 16 of the cylinder 10. The contact region 31 extends from a front end 18 to a rear end 19. The front section 20 of the contact region 31 directly adjoins the front end 18. If, starting from the front section 20 of the contact region 31, one moves further in the direction of the front end the syringe, there is no longer any contact there between the sealing element 17 and the inner wall 16 of the cylinder 10.

The plunger 11 is mounted in the cylinder 10 such that it, in the form of an initial movement from the rest state, can move a small amount in the direction of the front end of the syringe without the sealing element 17 following this movement. Only once a shoulder 21 butts against the rear end 19 of the sealing element 17 toward the end of the initial movement (see view B) is the sealing element 17 forced to follow a continued movement of the plunger 11.

A transmission element 22 extends between the front end 18 of the sealing element 17 and the plunger 11. The transmission element 22 includes an angle of approximately 45° with the longitudinal axis of the syringe and is connected to the sealing element 17 and the plunger 11 in a hinged fashion. With the initial movement of the plunger 11, the transmission element 22 is pulled forward and thereby exerts a tensile force on the front end 18 of the sealing element 17. As a result, the front end 18 of the sealing element 17 is pulled inward such that the sealing element 17 is lifted off from the inner wall 16 of the cylinder 10 in the front section 20 of the contact region 31. The contact pressure in the front section 20 of the contact region 31 reduces to zero and is therefore smaller than during the rest state. The front section 20 of the contact region 31 can be lifted off from the inner wall 16 over the whole circumference of the sealing element 17 by means of a multiplicity of transmission elements 22 distributed around the circumference of the plunger 11.

When the sealing element 17 has been lifted off from the inner wall 16 of the cylinder 10 with the front section 20 of the contact region 31, it is significantly easier to overcome the static friction between the sealing element 17 and the inner wall 16. In particular, there is a reduced risk of the sealing element 17 jamming with respect to the inner wall 16 and the force required for breaking free increasing even more as a result thereof. As a result of it being easier to set the sealing element 17 into motion, this results overall in a very uniform force build-up when, starting from the rest state, pressure is built-up on the pressure surface 14 of the plunger 11. First of all, it is easy to set the plunger 11 in motion. The transmission element 22 increasingly builds up a counter-tension until the shoulder 21 rests against the rear end 19 of the sealing element 17. Then it is possible to overcome the now reduced static friction between sealing element 17 and inner wall 16.

When no further pressure is exerted on the pressure surface 14 of the plunger 11 anymore, the movement of the plunger 11 stops. The sealing element 17, which was elastically deformed by the initial movement, returns to its initial state and, via the transmission element 22, again pulls the plunger 11 backward a little. The syringe is then once again situated in the rest state, from which the described process can restart from the beginning if required.

Figure 3:
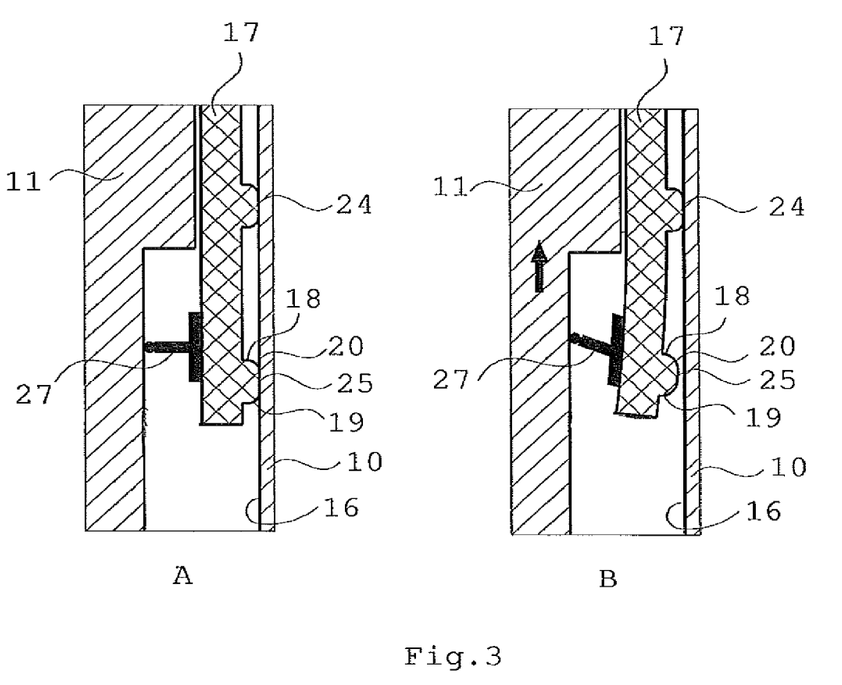

In the embodiment of FIG. 3, illustration A likewise shows the syringe in the rest state and illustration B likewise shows the syringe after the initial movement. The sealing element 17 has once against been designed such that it rests against the inner wall 16 of the cylinder 10 with sufficient contact pressure of its own accord. In this example, the sealing element 17 does not rest against the inner wall 16 over its whole length; rather, the contact is restricted to two separate contact regions 24, 25. The contact region 25 has a front end 18, a rear end 19 and a front section 20.

A transmission element 27 extends between the sealing element 17 and the plunger 11 and it is designed to pull the sealing element 17 inward such that the contact pressure reduces in the contact region 25 and, more particularly, in the front section 20 of the contact region 25. Depending on the design, the contact region 25 can be completely lifted off from the inner wall. If no pressure is exerted on the plunger 11 anymore, the sealing element 17 returns to the initial state from the elastically deformed state (illustration B) and thus also brings the plunger 11 back into the rest state via the transmission element 27. In this embodiment, the contact pressure is only reduced in the rear contact region 25 while the contact pressure in the front contact region 24 is not modified by the initial movement.

Figure 4:
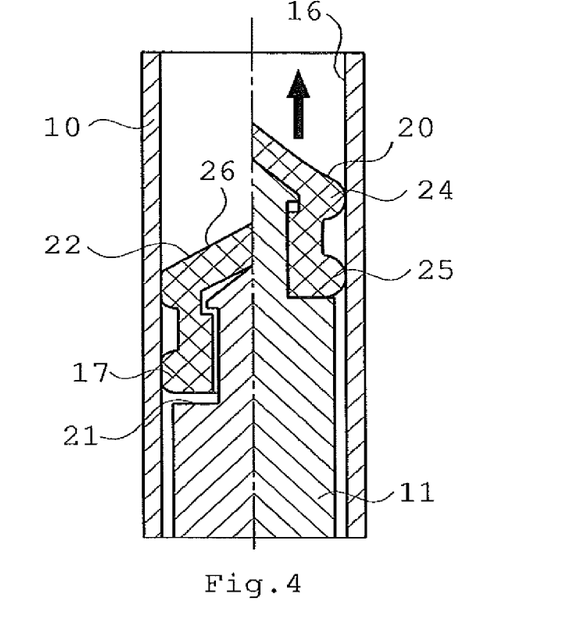

In the illustration of FIG. 4, which is split into two, the left half shows the syringe in the rest state and the right half shows the syringe during a movement that continues beyond the initial movement. The sealing element 17 extends around the plunger 11 and has two mutually separated contact regions 24, 25. The sealing element 17 is formed such that the contact regions 24, 25 rest against the inner wall 16 of the cylinder 10 with sufficient contact pressure of their own accord. A conical cap 26 which covers the front end of the plunger 11 is integrally connected to the sealing element 17. What the closed cap 26 achieves is that there are no further emergence paths except for the contact region between the sealing element 17 and cylinder 10. In the rest state, the tip of the plunger 11 rests against the cap 26 of the sealing element 17. Apart from the tip of the plunger 11, there is a clearance between the plunger 11 and the sealing element 17. This applies both to the outer region of the cap 26 and in the radial direction and to the distance between the shoulder 21 of the plunger 11 and the rear end of the sealing element 17.

When the plunger 11 performs an initial movement forward the tip of the cap 26 follows this movement such that the cap 26 acts as transmission element 22 and pulls the sealing element 17 inward in the contact region 24. The contact pressure in the front section 20 of the contact region 24 is reduced as a result. During the inward movement, the sealing element 17 uses the clearance existing in the rest state between the sealing element 17 and the plunger 11. The cap 26 with the sealing element 17 forms an elastic element which is put under tension by the initial movement.

Figure 5:
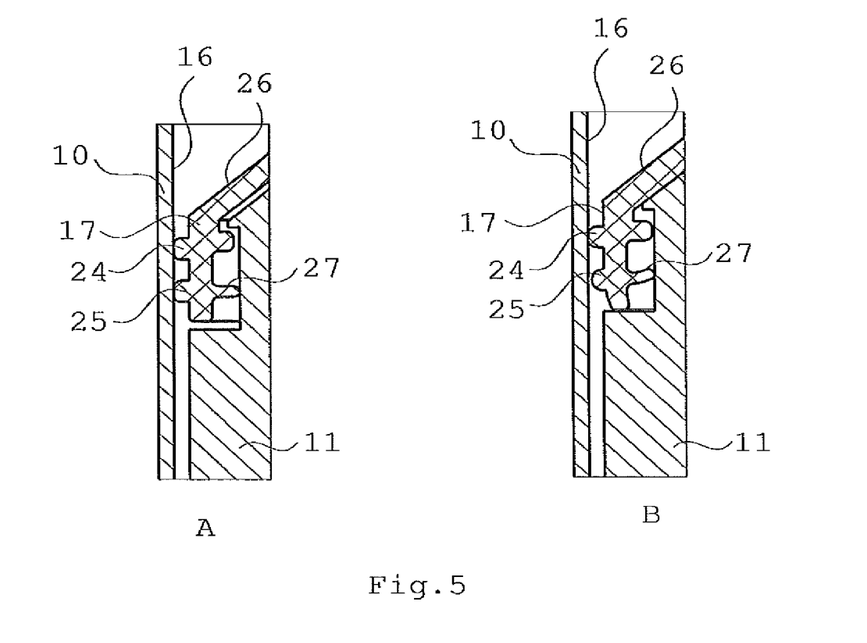

FIG. 5 illustrates a further embodiment of a syringe, wherein illustration A shows the rest state and illustration B shows the state after the initial movement of the plunger 11. This embodiment combines the features of FIGS. 3 and 4. The cap 26 acts as transmission element by means of which the contact pressure in the front section of the contact region 24 is reduced. A further transmission element 27 extends between the sealing element 17 and the plunger 11, by means of which the contact pressure in the front section of the contact region 25 is reduced by a tensile force, as in FIG. 3.

Figure 6:
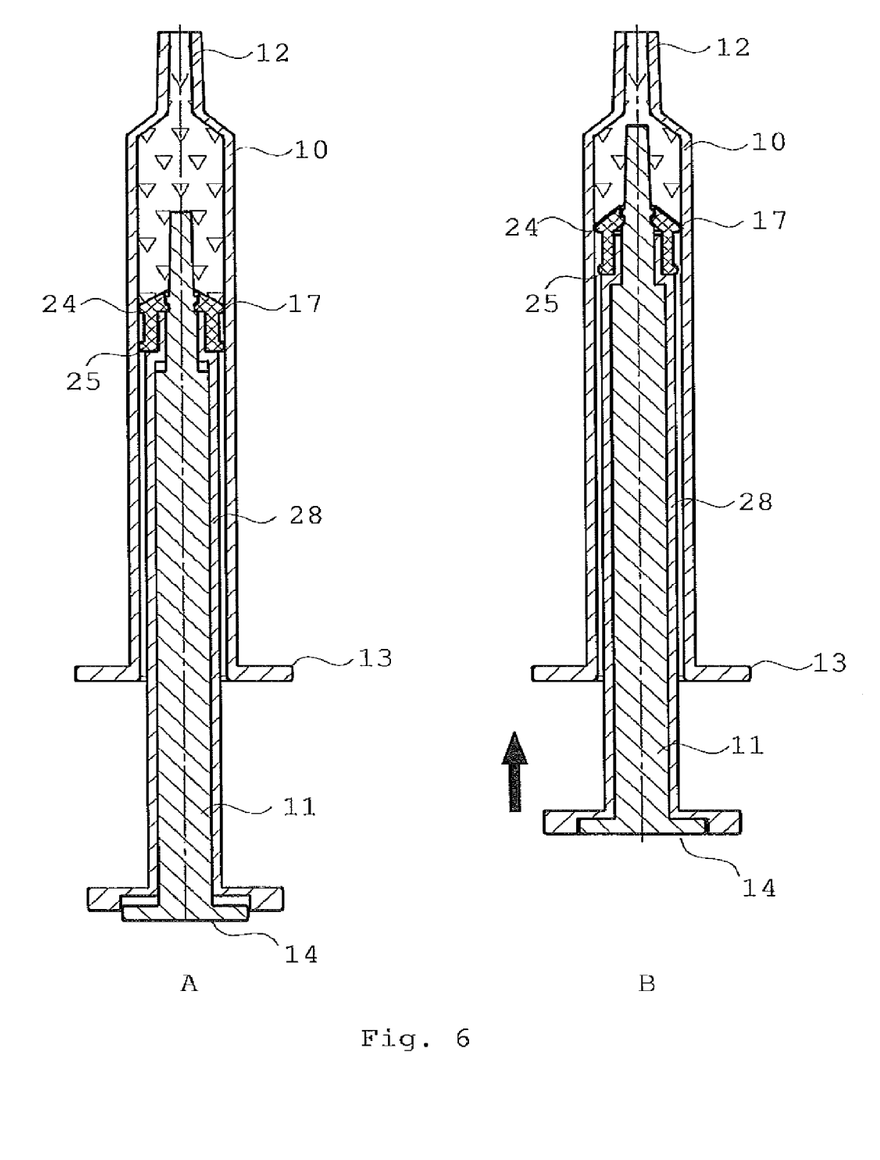
FIG. 6 shows two illustrations of a further embodiment of a syringe.

In the embodiment of FIG. 6, the syringe comprises a sleeve 28 which is arranged in the annular gap between the plunger 11 and the cylinder 10. The sleeve 28 serves to guide the sealing element 17. When the plunger 11 carries out an initial movement, the sleeve 28 does not move but rather initially remains in its position like the sealing element 17. Unlike FIG. 4, the front part of the sealing element 17 does not form a closed cap, but rather there is an aperture through which the front end of the plunger 11 extends. The front end of the plunger 11 is preferably fitted to the shape of the outlet 12 such that it is possible to empty the syringe completely.

The front end of the sealing element 17 is connected to the plunger 11 such that it follows the initial movement of the plunger 11. Like in FIG. 4, this movement is transmitted to the sealing element 17 as tensile force such that the contact pressure is reduced in the front part of the contact region 24. In the case of movement of the plunger 11 that continues beyond the initial movement, both the sealing element 17 and the sleeve 28 follow the movement of the plunger 11. Once no more pressure is exerted on the pressure surface 14, the movement of the plunger 11 ends. The sealing element 17 returns into the initial state from its elastically deformed state and, as a result, also moves the plunger 11 back into the position as per illustration A. In this embodiment, the shape-change of the sealing element is precisely defined and restricted since the plunger 11 can only cover a specific path in the sleeve 28.

Figure 7:
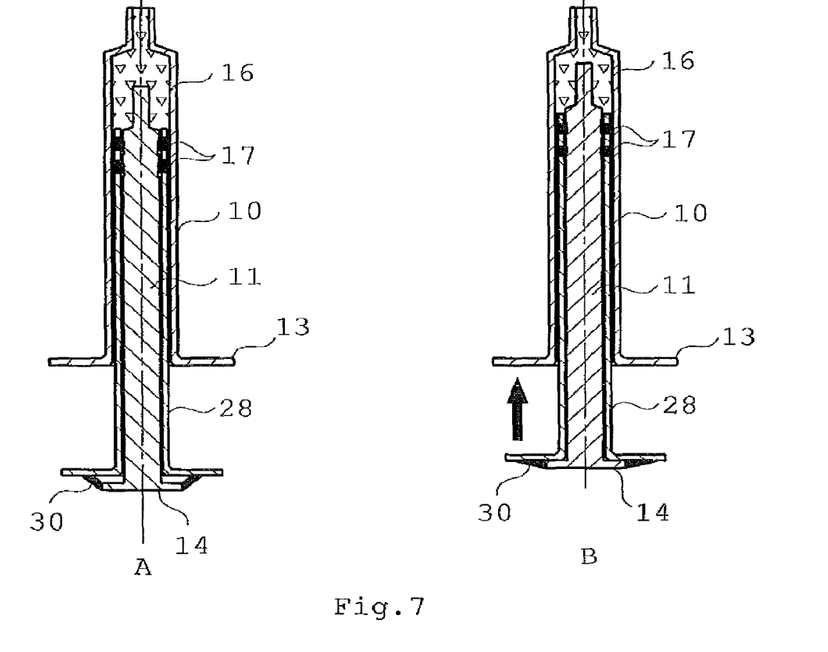
FIG. 7 shows the view from FIG. 6 in a further embodiment.

In the embodiment of FIG. 7, the syringe comprises two sealing elements 17, which in turn are guided by a sleeve 28. The plunger 11 is, as illustrated in the magnified illustration in FIG. 8, shaped such that, in the rest state (illustration A), it exerts a radially outwardly directed force on the sealing elements 17. As a result of this force, the sealing elements 17 rest against the inner wall 16 of the cylinder 10 with sufficient contact pressure in the rest state.

Figure 8:
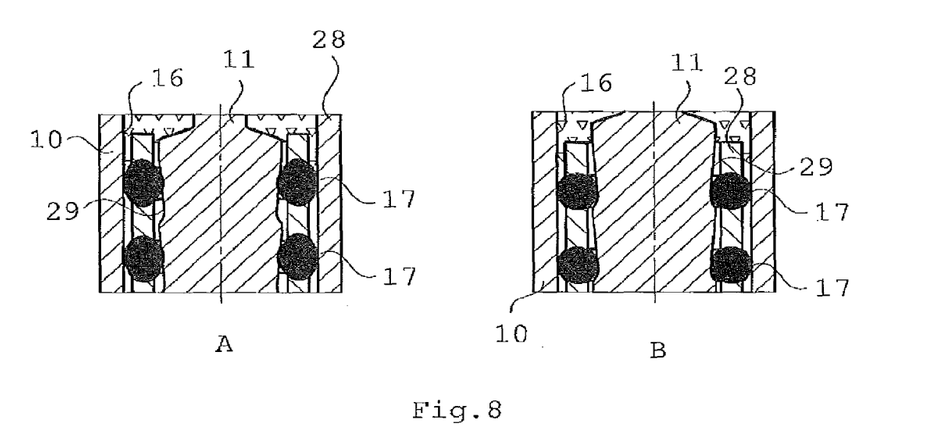
FIG. 8 shows detailed views from FIG. 7.

In the case of an initial movement of the plunger 11, the sealing elements 17 move along a conical surface 29 of the plunger 11 such that the contact pressure is reduced in the contact region between the sealing ring and the cylinder, and more particularly in the front section of the contact region. The plunger 11 is connected to the sleeve 28 via a spring element 30. The spring element 30 is tensioned during the initial movement of the plunger 11. When pressure is no longer exerted on the plunger 11, the spring element 30 relaxes again and pulls the plunger 11 relative to the sealing element 17 and the sleeve 28 back into the rest state as per illustration A. As a result, the sufficient contact pressure between the sealing elements 17 and the inner wall 16 of the cylinder 10 is built up again. From this initial state, the plunger 11 can carry out a new initial movement, by means of which the contact pressure between the sealing elements 17 and the inner wall 16 is reduced.

The invention claimed is:

1. A syringe with a cylinder, with a plunger arranged within the cylinder and with a sealing element, which rests against an inner wall of the cylinder with a contact region and seals an annular gap between the plunger and the inner wall of the cylinder, wherein the contact region has a front section, which, in a rest state, rests against the inner wall of the cylinder with contact pressure, and wherein the plunger is connected to the sealing element such that the sealing element does not follow an initial movement of the plunger from the rest state and that the sealing element follows a continued movement of the plunger, characterized in that the contact pressure between the front section of the contact region and the inner wall is reduced during the initial movement and the contact region being partially lifted off from the inner wall.

2. The syringe as claimed in claim 1, characterized in that, in the rest state, there is a clearance between the sealing element and the plunger and in that the sealing element moves into the clearance during the initial movement of the plunger.

3. The syringe as claimed in claim 1, characterized in that a sleeve arranged between the plunger and the cylinder is provided for guiding the sealing element.

4. The syringe as claimed in claim 1, characterized in that it comprises an elastic element which is tensioned with the initial movement of the plunger.

5. The syringe as claimed in claim 1, characterized in that a sleeve arranged between the plunger and the cylinder is provided for guiding the sealing element and an elastic element which is tensioned with the initial movement of the plunger is arranged between the plunger and the sleeve.

6. The syringe as claimed in claim 1, characterized in that a static friction between the contact region and the inner wall of the cylinder after the initial movement has reduced by at least 20% compared to in the rest state.

7. The syringe as claimed in claim 1, characterized in that a static friction between the contact region and the inner wall of the cylinder after the initial movement has reduced by at least 30% compared to in the rest state.

8. The syringe as claimed in claim 1, characterized in that a radially outwardly directed force acts on the sealing element in the rest state of the plunger.

9. The syringe as claimed in claim 8, characterized in that, during the initial movement, the sealing element moves along a conical surface of the plunger such that the contact pressure reduces.

10. The syringe as claimed in claim 1, characterized in that a static friction between the contact region and the inner wall of the cylinder after the initial movement has reduced by at least 10% compared to in the rest state.

11. The syringe as claimed in claim 10, characterized in that a radially outwardly directed force acts on the sealing element in the rest state of the plunger.

12. The syringe as claimed in claim 10, characterized in that, in the rest state, there is a clearance between the sealing element and the plunger and in that the sealing element moves into the clearance during the initial movement of the plunger.

13. The syringe as claimed in claim 1, characterized in that provision is made for a transmission element between the plunger and the sealing element and in that the transmission element is used to transmit a force onto the sealing element during the initial movement of the plunger, said force reducing the contact pressure.

14. The syringe as claimed in claim 13, characterized in that a static friction between the contact region and the inner wall of the cylinder after the initial movement has reduced by at least 10% compared to in the rest state.

15. The syringe as claimed in claim 13, characterized in that a radially outwardly directed force acts on the sealing element in the rest state of the plunger.

16. The syringe as claimed in claim 13, characterized in that, in the rest state, there is a clearance between the sealing element and the plunger and in that the sealing element moves into the clearance during the initial movement of the plunger.

17. The syringe as claimed in claim 13, characterized in that the transmission element is designed to transmit a tensile force onto the sealing element.

18. The syringe as claimed in claim 17, characterized in that a static friction between the contact region and the inner wall of the cylinder after the initial movement has reduced by at least 10% compared to in the rest state.

19. The syringe as claimed in claim 17, characterized in that a radially outwardly directed force acts on the sealing element in the rest state of the plunger.

20. The syringe as claimed in claim 17, characterized in that, in the rest state, there is a clearance between the sealing element and the plunger and in that the sealing element moves into the clearance during the initial movement of the plunger.

\* \* \* \* \*